(12) United States Patent
Emery

(10) Patent No.: US 11,131,310 B1
(45) Date of Patent: Sep. 28, 2021

(54) AIRFLOW ASSEMBLY

(71) Applicant: Eric D. Emery, Lake Barrington Shores, IL (US)

(72) Inventor: Eric D. Emery, Lake Barrington Shores, IL (US)

(*) Notice: Subject to any disclaimer, the term of this patent is extended or adjusted under 35 U.S.C. 154(b) by 549 days.

(21) Appl. No.: 15/451,965

(22) Filed: Mar. 7, 2017

(51) Int. Cl.
| | |
|---|---|
| *F04D 25/08* | (2006.01) |
| *F04D 25/06* | (2006.01) |
| *F04D 29/42* | (2006.01) |
| *F04D 29/70* | (2006.01) |
| *A42B 1/008* | (2021.01) |
| *A42B 3/28* | (2006.01) |
| *A61F 9/06* | (2006.01) |
| *F41H 1/04* | (2006.01) |
| *F04D 17/16* | (2006.01) |
| *F04D 29/62* | (2006.01) |
| *H02J 7/35* | (2006.01) |
| *A42B 1/0182* | (2021.01) |

(52) U.S. Cl.
CPC .............. *F04D 25/08* (2013.01); *A42B 1/008* (2013.01); *A42B 1/0182* (2021.01); *A42B 3/286* (2013.01); *A61F 9/068* (2013.01); *F04D 17/16* (2013.01); *F04D 25/0673* (2013.01); *F04D 29/4226* (2013.01); *F04D 29/624* (2013.01); *F04D 29/703* (2013.01); *F41H 1/04* (2013.01); *H02J 7/35* (2013.01)

(58) Field of Classification Search
CPC .... F04D 25/08; F04D 29/4226; F04D 29/703; F04D 17/16; F04D 25/0673; F04D 29/624; A42B 1/008; A42B 1/062; A42B 3/28; A42B 3/286; A42C 5/04; A45D 20/20; A45D 20/22; A45D 20/44; H02J 7/35; F41H 1/04; A61F 9/068
USPC ......... 454/66, 251, 239; 2/7, 6.1, 171.3, 411
See application file for complete search history.

(56) References Cited

U.S. PATENT DOCUMENTS

| | | | |
|---|---|---|---|
| 2,469,273 A | 5/1949 | Parker | |
| 3,112,745 A | 12/1963 | Boyer | |
| 3,496,854 A * | 2/1970 | Hill ........................... | A42B 3/28 2/410 |
| 3,535,707 A * | 10/1970 | Greenlee ................. | A61F 9/068 128/200.27 |
| 3,629,868 A | 12/1971 | Greenlee | |
| 3,649,964 A | 3/1972 | Schoelz et al. | |
| 3,881,478 A | 5/1975 | Rosendahl et al. | |
| 4,280,491 A * | 7/1981 | Berg ...................... | A42B 3/225 128/201.24 |
| 4,309,774 A | 1/1982 | Guzowski | |
| 4,462,399 A * | 7/1984 | Braun .................. | A62B 18/045 128/201.24 |
| 4,672,968 A | 6/1987 | Lenox et al. | |
| 5,003,866 A * | 4/1991 | Ricci .................. | B60H 1/00464 454/136 |

(Continued)

FOREIGN PATENT DOCUMENTS

WO 2010075397 7/2010

*Primary Examiner* — Jessica Yuen

(57) ABSTRACT

An airflow assembly with a lightweight airflow mechanism; which is both portable with self-contained power; and easily mounted on various types of head gear; ranging from welding masks, hardhats, police and other first responder helmets, military helmets, baseball caps, cloth hats and other headgear; in order to complete the airflow assembly, provides the mounting of the airflow assembly on the headgear to be permanent or releasable or portable.

7 Claims, 9 Drawing Sheets

(56) References Cited

U.S. PATENT DOCUMENTS

| | | | |
|---|---|---|---|
| 5,031,237 A | 7/1991 | Honrud | |
| 5,123,114 A | 6/1992 | Desanti | |
| 5,156,568 A * | 10/1992 | Ricci | B60H 1/00464 |
| | | | 454/129 |
| 5,193,347 A | 3/1993 | Aplsdorf | |
| 5,561,855 A | 10/1996 | McFall | |
| 5,577,495 A | 11/1996 | Murphy | |
| 5,839,121 A * | 11/1998 | Morales | A42B 3/281 |
| | | | 2/7 |
| 5,878,742 A | 3/1999 | Figueredo et al. | |
| 5,896,579 A | 4/1999 | Johnson et al. | |
| RE36,242 E | 6/1999 | Aplsdorf | |
| 6,032,291 A * | 3/2000 | Asenguah | A42B 1/008 |
| | | | 2/171.3 |
| 6,374,823 B1 | 4/2002 | Hajianpour | |
| 6,598,236 B1 * | 7/2003 | Gantt | A42B 1/008 |
| | | | 132/53 |
| 6,645,064 B1 * | 11/2003 | Werjefelt | B64D 45/00 |
| | | | 244/118.5 |
| 6,836,906 B2 * | 1/2005 | Holmes | A42B 3/22 |
| | | | 128/200.28 |
| 6,990,691 B2 | 1/2006 | Klotz et al. | |
| 7,178,932 B1 | 2/2007 | Buckman | |
| 7,200,873 B2 | 4/2007 | Klotz et al. | |
| 7,244,106 B2 | 7/2007 | Kallman et al. | |
| 7,534,005 B1 | 5/2009 | Buckman | |
| 7,752,682 B2 | 7/2010 | VanDerWoude et al. | |
| 7,937,775 B2 | 5/2011 | Manzella, Jr. et al. | |
| 7,937,779 B2 | 5/2011 | Klotz et al. | |
| 8,196,224 B2 | 6/2012 | Manzella, Jr. et al. | |
| 8,336,113 B2 | 12/2012 | Uttrachi | |
| 8,407,818 B2 | 4/2013 | VanDerWoude et al. | |
| 8,534,279 B2 * | 9/2013 | Brace | A62B 18/045 |
| | | | 128/201.15 |
| 8,756,715 B1 | 6/2014 | Moffitt, Jr. | |
| 8,955,168 B2 | 2/2015 | Manzella, Jr. et al. | |
| 9,155,923 B2 * | 10/2015 | Proctor | A62B 18/02 |
| 9,486,026 B1 * | 11/2016 | Cook, Sr. | A42B 1/24 |
| 9,700,743 B2 * | 7/2017 | Castiglione | A62B 9/04 |
| 9,744,493 B2 * | 8/2017 | Legare | A62B 23/02 |
| 2007/0238405 A1 * | 10/2007 | Arai | A42B 3/283 |
| | | | 454/121 |
| 2009/0055987 A1 | 3/2009 | Becker et al. | |
| 2009/0210989 A1 | 8/2009 | Becker et al. | |
| 2010/0000007 A1 * | 1/2010 | Wood | A42B 1/008 |
| | | | 2/171.3 |
| 2010/0005572 A1 * | 1/2010 | Chaplin | A42B 3/285 |
| | | | 2/411 |
| 2011/0041237 A1 * | 2/2011 | Gupta | A42B 1/008 |
| | | | 2/171.3 |
| 2011/0105013 A1 * | 5/2011 | Tseng | A42B 3/245 |
| | | | 454/251 |
| 2011/0105014 A1 * | 5/2011 | Tseng | A42B 3/245 |
| | | | 454/251 |
| 2011/0231977 A1 * | 9/2011 | Rupnick | A42B 3/286 |
| | | | 2/7 |
| 2013/0263364 A1 * | 10/2013 | Green | A42B 3/286 |
| | | | 2/422 |
| 2013/0312151 A1 * | 11/2013 | North | A61F 9/06 |
| | | | 2/8.2 |
| 2015/0157818 A1 * | 6/2015 | Darby | F04D 29/281 |
| | | | 128/201.13 |
| 2015/0182381 A1 * | 7/2015 | Davis | A61F 9/068 |
| | | | 2/8.6 |
| 2016/0079762 A1 * | 3/2016 | Wang | H02J 50/12 |
| | | | 307/104 |
| 2017/0135490 A1 * | 5/2017 | Andrix | H02J 7/0042 |
| 2018/0014597 A1 * | 1/2018 | Cooke | A42B 3/042 |
| 2018/0064199 A1 * | 3/2018 | Battis | A42B 3/286 |

\* cited by examiner

AIRFLOW ASSEMBLY

This invention relates to an airflow assembly; and more particularly to an airflow assembly having a headgear of various types capable of cooling a person wearing the headgear due to a fan being releasably or permanently attached to the headgear to form the airflow assembly.

BACKGROUND OF THE INVENTION

With various types of headgear, it is very desirable to create or provide an airflow through the headgear in order to make the person wearing that headgear more comfortable, and even most likely safer. The airflow can be created by a fan.

Unfortunately, the prior art is directed to a fan connection for headgear, that is not portable. Such a fan connection restricts how a person wearing the headgear with that fan connection can move. That movement restriction can easily interfere with a job; which requires either moving from one place to another, lifting material for use on the job or other actions requiring physical dexterity and mobility.

Accordingly, many attempts to make a portable fan for headgear are known. However, those attempts result in a bulky, cumbersome fan. That structure interferes with the proper function of the headgear. Furthermore, such a fan can interfere with work required to be done, while wearing the headgear.

Also, the bulky, cumbersome fan fails to have sufficient power to last a long period of time. This defect makes the fan ineffective for use on a job. If a cooling device, which is portable, has power for a long period of time, adds little weight to the headgear, and is easily moved from one type of headgear to another; can be developed; great advantages can be obtained. This is especially useful if the cooling device is easily moved from one type of headgear to another.

SUMMARY OF THE INVENTION

Among the many objectives of this invention is the provision of an airflow assembly with a lightweight airflow mechanism, which may be attached to or removed from a headgear as desired.

A further objective of this invention is the provision of an airflow assembly with a lightweight airflow mechanism and power source, which may be attached to a welding mask.

A still further objective of this invention is the provision of an airflow assembly with a lightweight airflow mechanism and power source, which may be attached to a hard hat.

Yet a further objective of this invention is the provision of an airflow assembly with a lightweight airflow mechanism and power source, which may be attached to a cloth hat.

Another objective of this invention is the provision of an airflow assembly with a battery powered, lightweight fan, which may be attached to a welding mask.

Yet another objective of this invention is the provision of an airflow assembly with a battery powered, lightweight fan, which may be attached to a hard hat.

Still another objective of this invention is the provision of an airflow assembly with a battery powered, lightweight fan, which may be attached to a cloth hat.

Also an objective of this invention is the provision of an airflow assembly with a battery powered, lightweight fan, which may be releasably attached to a welding mask.

A further objective of this invention is the provision of an airflow assembly with a battery powered, lightweight fan, which may be releasably attached to a hard hat.

Yet a further objective of this invention is the provision of an airflow assembly with a battery powered, lightweight fan, which may be releasably attached to a cloth hat.

Still a further objective of this invention is the provision of an airflow assembly with a battery powered, lightweight fan, wherein the battery is rechargeable.

These and other objectives of the invention (which other objectives become clear by consideration of the specification, claims and drawings as a whole) are met by providing an airflow assembly with a lightweight airflow mechanism; which is both portable with self-contained power; and easily mounted on various types of head gear; ranging from welding masks, hardhats, police and other first responder helmets, military helmets, baseball caps, cloth hats and other headgear; in order to complete the airflow assembly, the mounting of the airflow assembly on the headgear, being permanent or releasable or portable.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

Figure 1:
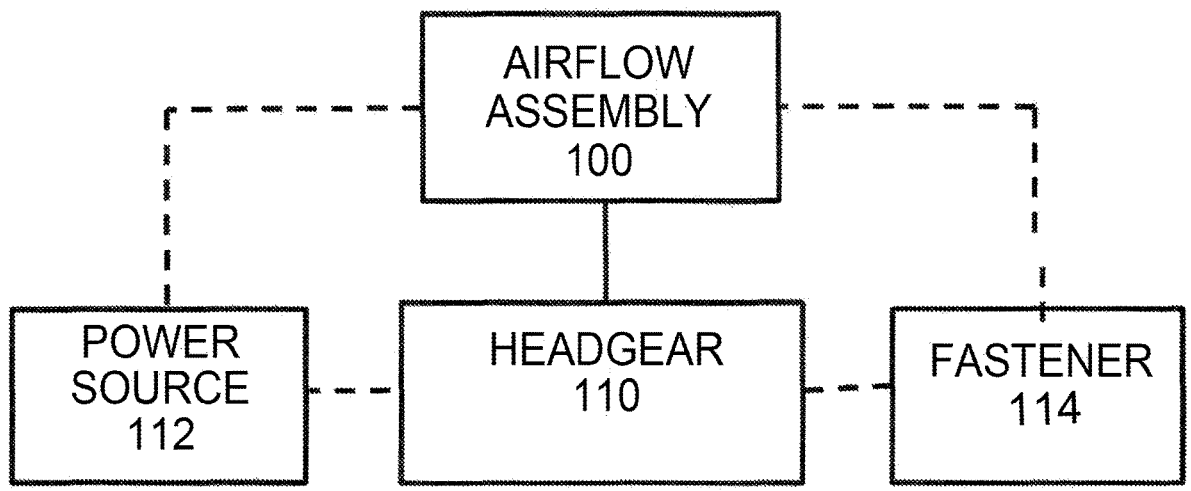
FIG. 1 depicts a block diagram of the airflow assembly 100 of this invention.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, may be used with respect to the drawings. These and similar to directional terms are not to be construed to limit the scope of the invention in any manner. The words attach, connect, couple, and similar terms with their inflectional morphemes do not necessarily denote direct or intermediate connections, but may also include connections through mediate elements or devices.

An airflow assembly of this invention uses a fan with a durable power source in combination with a headgear. The headgear can be any suitable protective headgear including a hard headgear or a soft headgear. The fan and durable power source have both a small size and a low weight, which permits the attachment thereof almost any type of headgear. Such a structure is especially useful on a welding mask, a first responder helmet, a baseball cap or other headgear.

Referring now to FIG. 1, the airflow assembly 100 includes headgear 110 cooperating with an airflow mechanism 130. The airflow mechanism 130 permits a flow of air between the headgear and the head of the person wearing the same.

Figure 2:
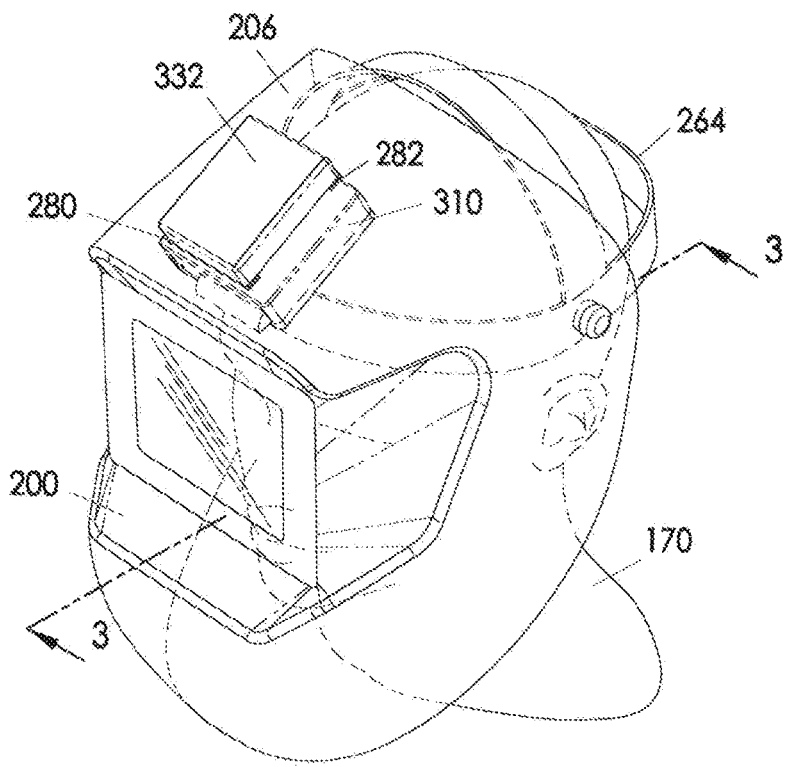
FIG. 2 depicts a perspective of view of the airflow assembly 100 of this invention in the form of a welding mask 200 with a wireless battery assembly 280 and first fan assembly 308 attached thereto.
Figure 3:
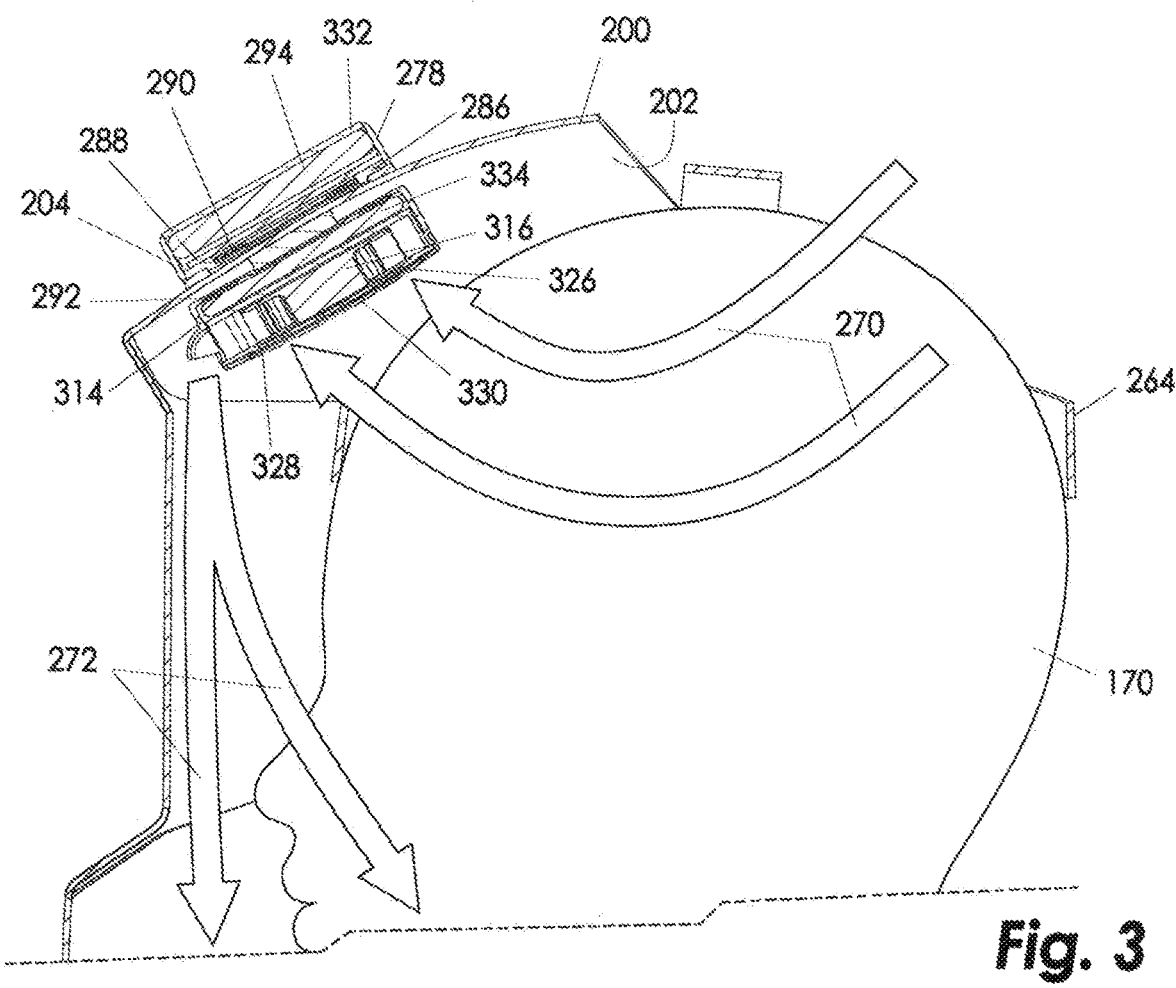
FIG. 3 depicts a side, cross-sectioned view of the welding mask 200 with a wireless battery assembly 280 and first fan assembly 308 attached thereto, based on Line 3-3 of FIG. 2.

Now referring to FIG. 2 and FIG. 3, the headgear 110 of FIG. 1 becomes welding mask 200. The airflow mechanism 130 of FIG. 1 becomes first fan assembly 308 in FIG. 2 and FIG. 3. First fan assembly 308 is substantially contained within fan housing 310. Fan housing 310 is attached to the mask interior 202 of the welding mask 200 by a fan fastener 312 (FIG. 8), while the wireless battery assembly 280 is attached to the mask exterior 206 of the welding mask 200 by a battery fastener 282 (FIG. 9). Solar panel 332 may be attached to the exterior face 284 of the battery housing 278 for the wireless battery assembly 280.

Fan fastener 312 (FIG. 8) and battery fastener 282 (FIG. 9) may be any suitable fastener. Two preferred fasteners are a hook and loop assembly or a magnet. A standard hook and loop assembly is available under the registered trademark VELCRO, owned by Velcro Industries B.V. LIMITED LIABILITY COMPANY NETHERLANDS Castorweg 22-24 Curacao NETHERLANDS ANTILLES. An especially preferred magnet is a neodymium magnet. This preference is created by the strength and lightweight characteristics of the neodymium magnet, as well as the minimal interference between the wireless battery assembly 280 and the fan assembly 308, while providing effective cooperation, so that the airflow assembly 100 functions properly.

In FIG. 3, the function of air flow assembly 100 becomes even more clear. The operation of fan assembly 308, contained within fan housing 310 causes an increased air intake 270 and air output 272. The air intake 270 of welding mask 200 may be increased by oscillation of blower fan 316, which causes air intake 270 to pass air through top fan cover 330, then filter compartment 326, and then filter medium 328, when the air finally passes more efficiently to air output 272. The oscillation of blower fan 316 is powered by fan battery 334 and receiving coil 292 which are both attached to the fan housing interior (FIG. 8) 340 of the bottom fan cover 314. The fan housing exterior 344 (FIG. 8) of the bottom fan cover 314 is attached to the mask interior 202 of the welding mask 200.

With further reference to FIG. 3, the wireless battery assembly 280 attaches to the exterior of the welding mask 200 transmits power for operation of first fan assembly 308 by the transmitting coil 290. The transmitting coil 290 is housed within battery cover top 284 and battery cover bottom 286. The battery cover top 284 and battery cover bottom 286 also has shield 288 situated within, in order to provide stability and protection. The battery 294 is positioned within battery top cover 204. The fan assembly 308 (FIG. 4) may also be powered by a solar panel 332 attached to the exterior face 284 of the external battery cover 294. That is to say the solar panel 332 may recharge or maintain a charge battery 294.

Figure 4:
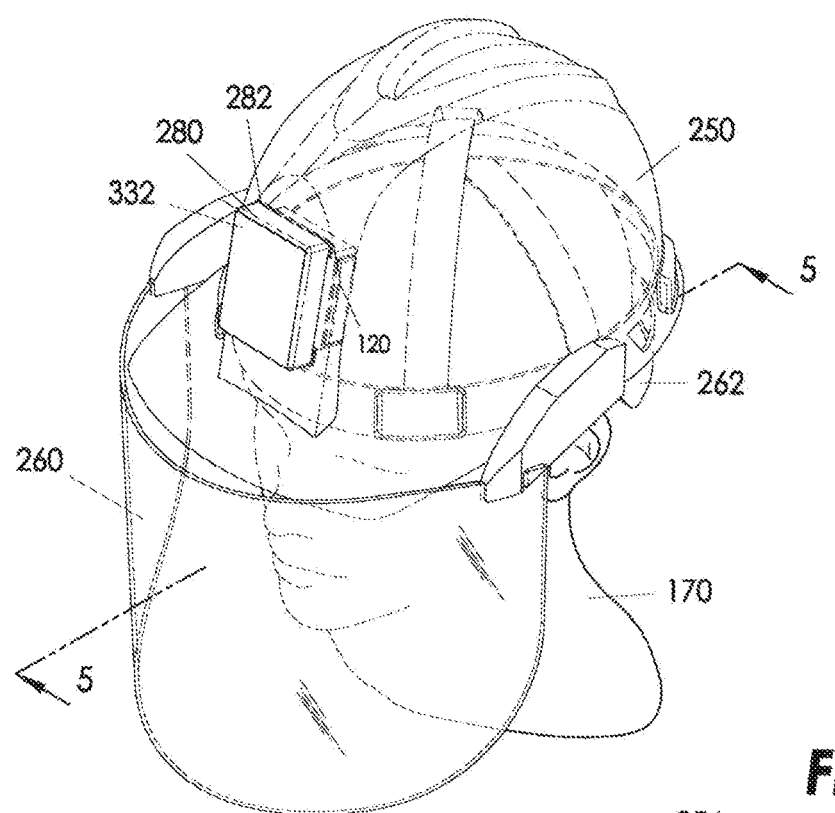
FIG. 4 depicts a perspective of view of the airflow assembly 100 of this invention in the form of a hardhat 250 having a visor 260 with a first fan assembly 308 and wireless battery assembly 280 attached to the hardhat 250.
Figure 5:
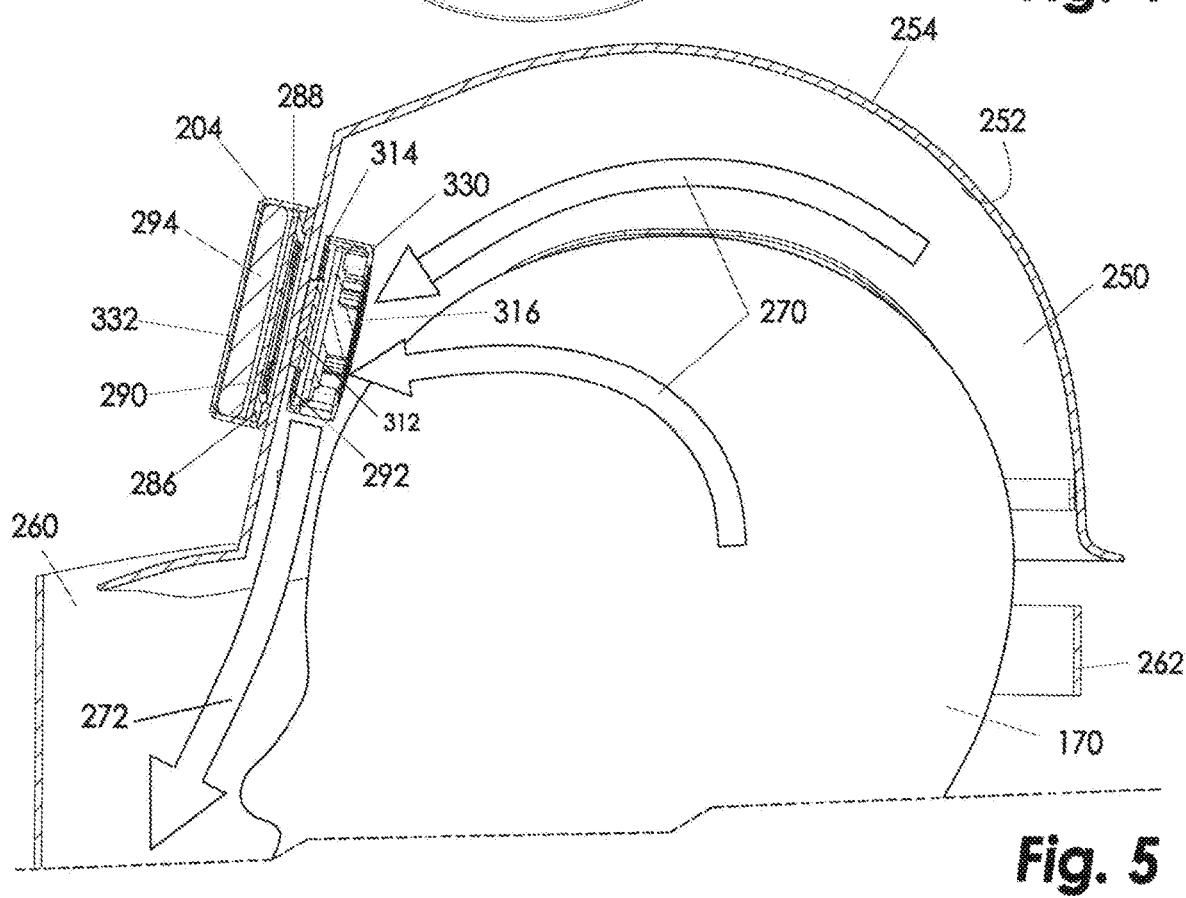
FIG. 5 depicts a side, cross-sectioned view of hardhat 250 having a visor 260 with a first fan assembly 308 and wireless battery assembly 280 attached to the hardhat 250, based on Line 5-5 of FIG. 4.

Adding FIG. 4 and FIG. 5 to the consideration, a hardhat 250 may form part of the airflow assembly 100 hat interior 252 and hat exterior 254. Operation of fan assembly 310 causes increased air intake 270 and air output 272. Fan assembly 310 includes a blower fan 316 communicating sequentially with top fan cover 330, then filter compartment 326, followed by filter medium 328.

The air intake 270 of hardhat 250 with visor 260 is increased by oscillation of blower fan 316, which causes air intake 270 to pass through top fan cover 330, then filter compartment 326, then filter medium 328, and finally passed more efficiently to air output 272. The oscillation of blower fan 316 is powered by fan battery 334 and receiving coil 292 which are both attached to the interior of the bottom fan cover 314. The exterior of the bottom fan cover 314 is attached to the hat interior 252 of the hardhat 250 with visor 260.

Figure 6:
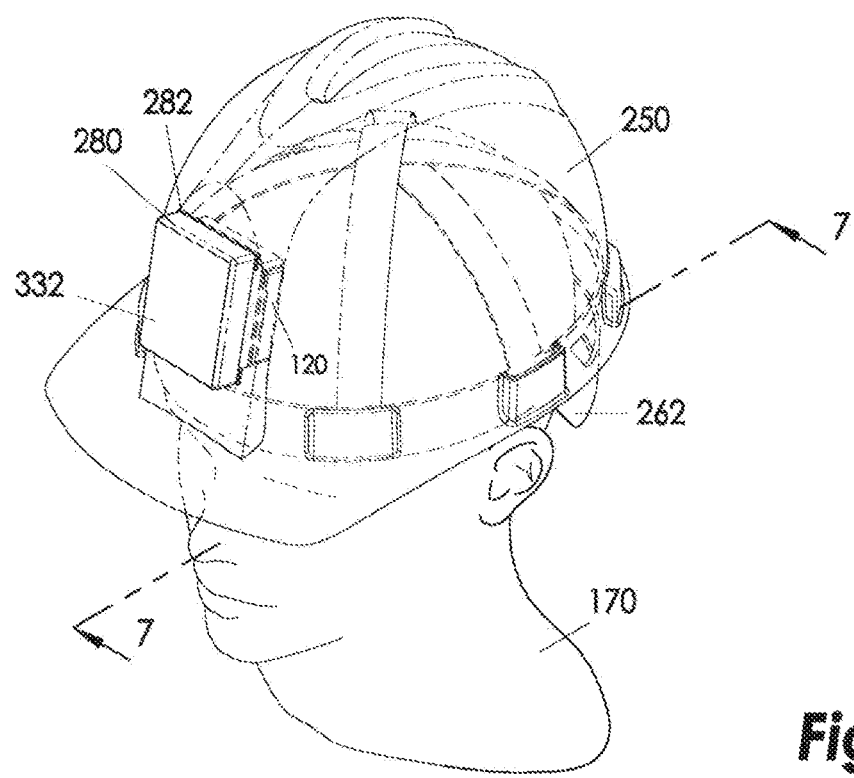
FIG. 6 depicts a perspective of view of the airflow assembly 100 of this invention in the form of a hardhat 250 with a first fan assembly 308 and wireless battery assembly 280 attached to the hardhat 250.
Figure 7:
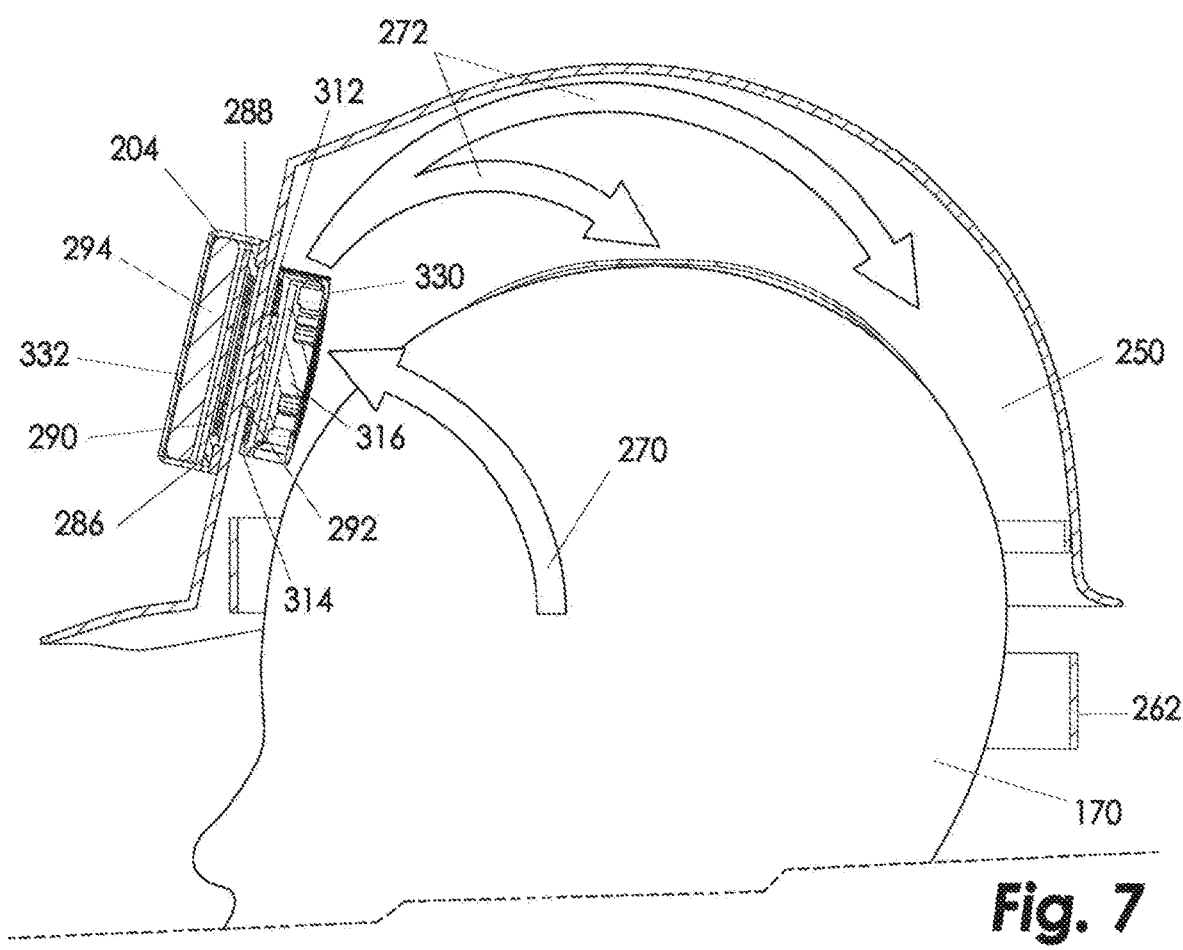
FIG. 7 depicts a side, cross-sectioned view of hardhat 250 with a first fan assembly 308 and a wireless battery assembly 280 attached to the hardhat 250, based on Line 7-7 of FIG. 6.

FIG. 6 and FIG. 7 add to the consideration by showing hardhat 250 without the visor 260. Operation of fan assembly 310 causes increased air intake 270 and air output 272. The air intake 270 of hardhat 250 is increased by oscillation of blower fan 316, which causes air intake 270 to pass through top fan cover 330, then filter compartment 326, then filter medium 328, and finally passed more efficiently to air output 272. The oscillation of blower fan 316 is powered by fan battery 334 and receiving coil 292 which are both contained within the interior of the bottom fan cover 314. The exterior of the bottom fan cover 314 is attached to the interior of the hardhat 250.

Figure 8:
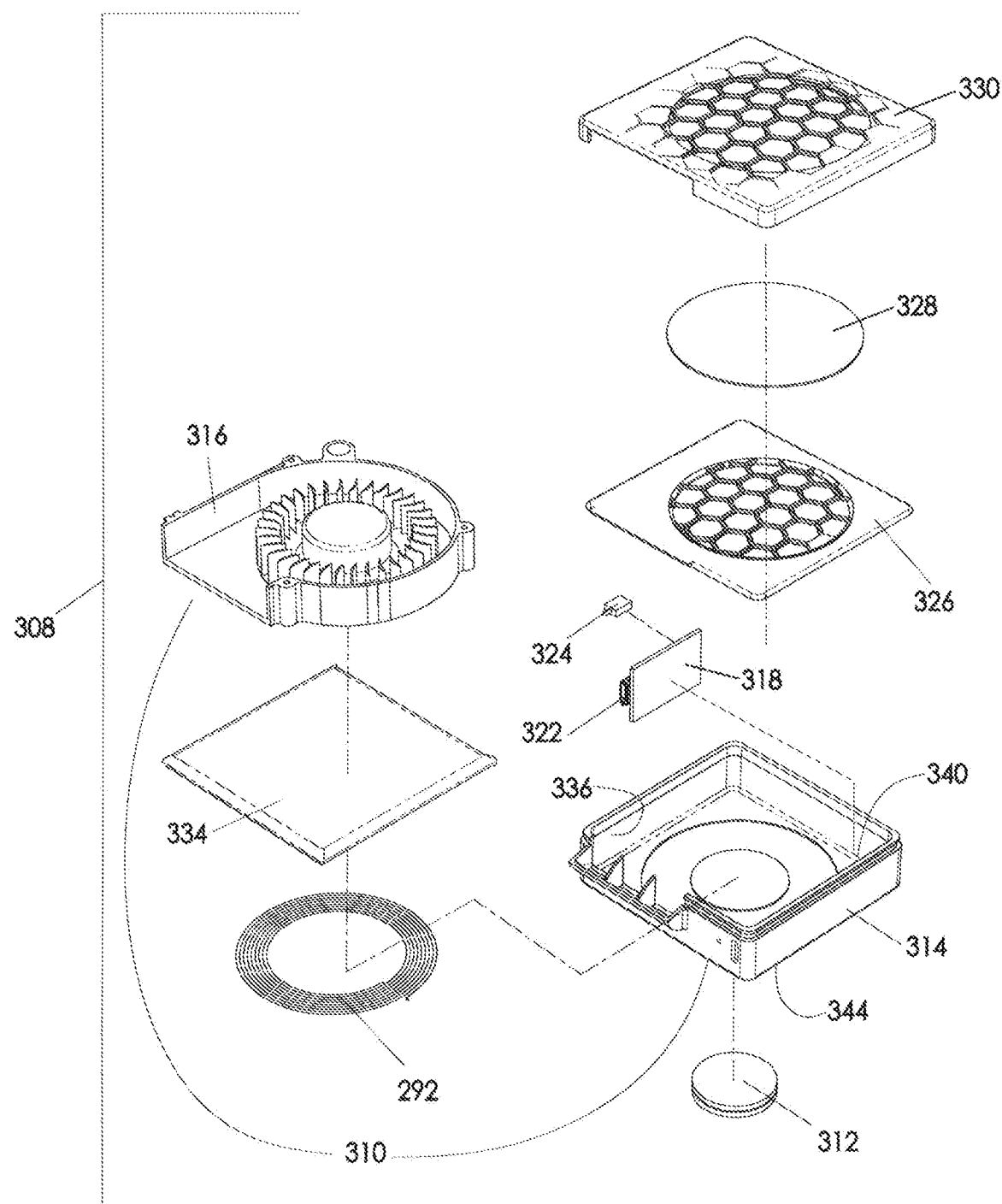
FIG. 8 depicts an exploded, perspective view of a first fan assembly 308 in fan housing 310 for use with the airflow assembly 100 of this invention.
Figure 9:
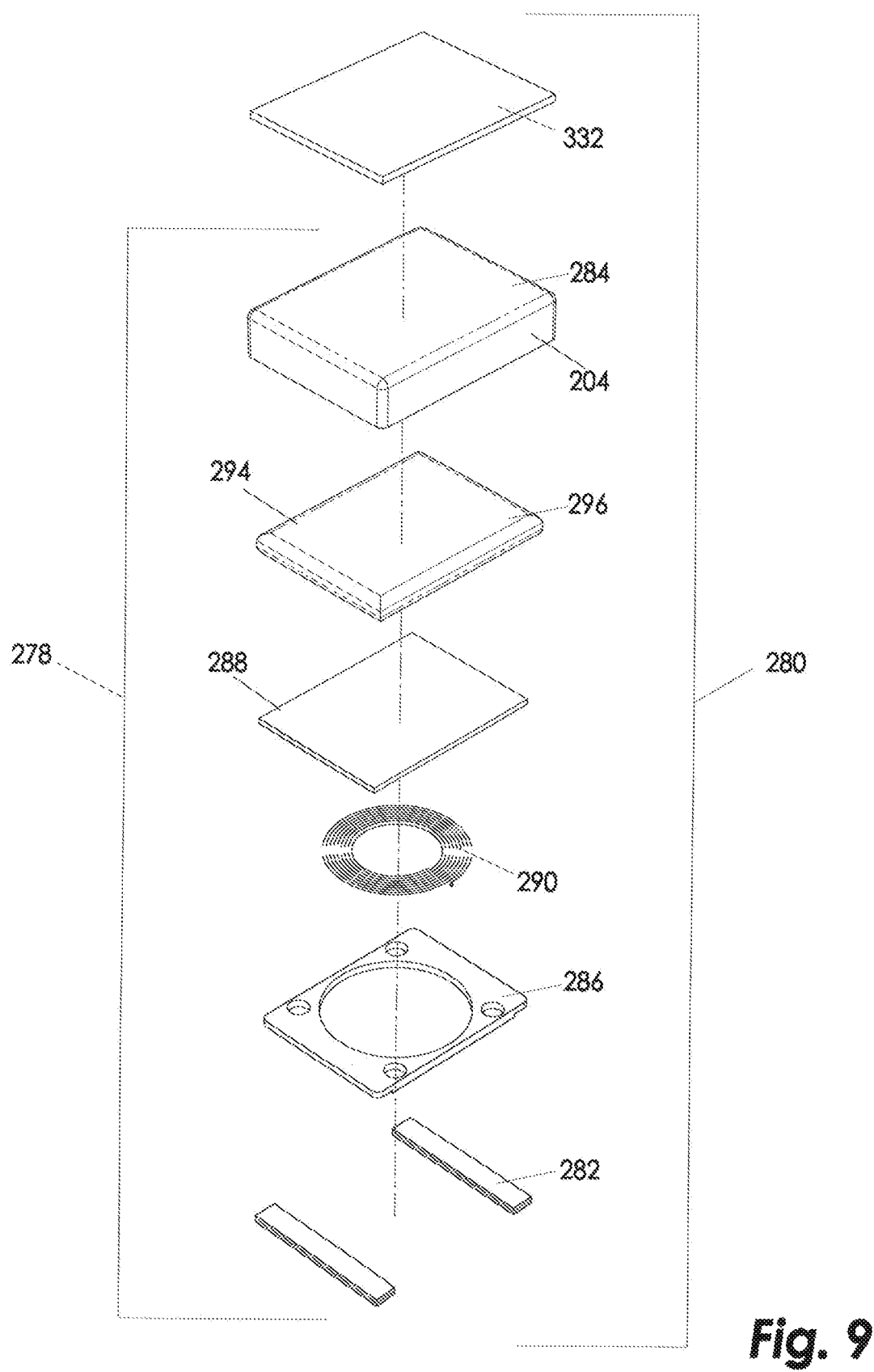
FIG. 9 depicts an exploded, perspective view of a battery assembly 280 for use with the airflow assembly 100 of this invention.
Figure 10:
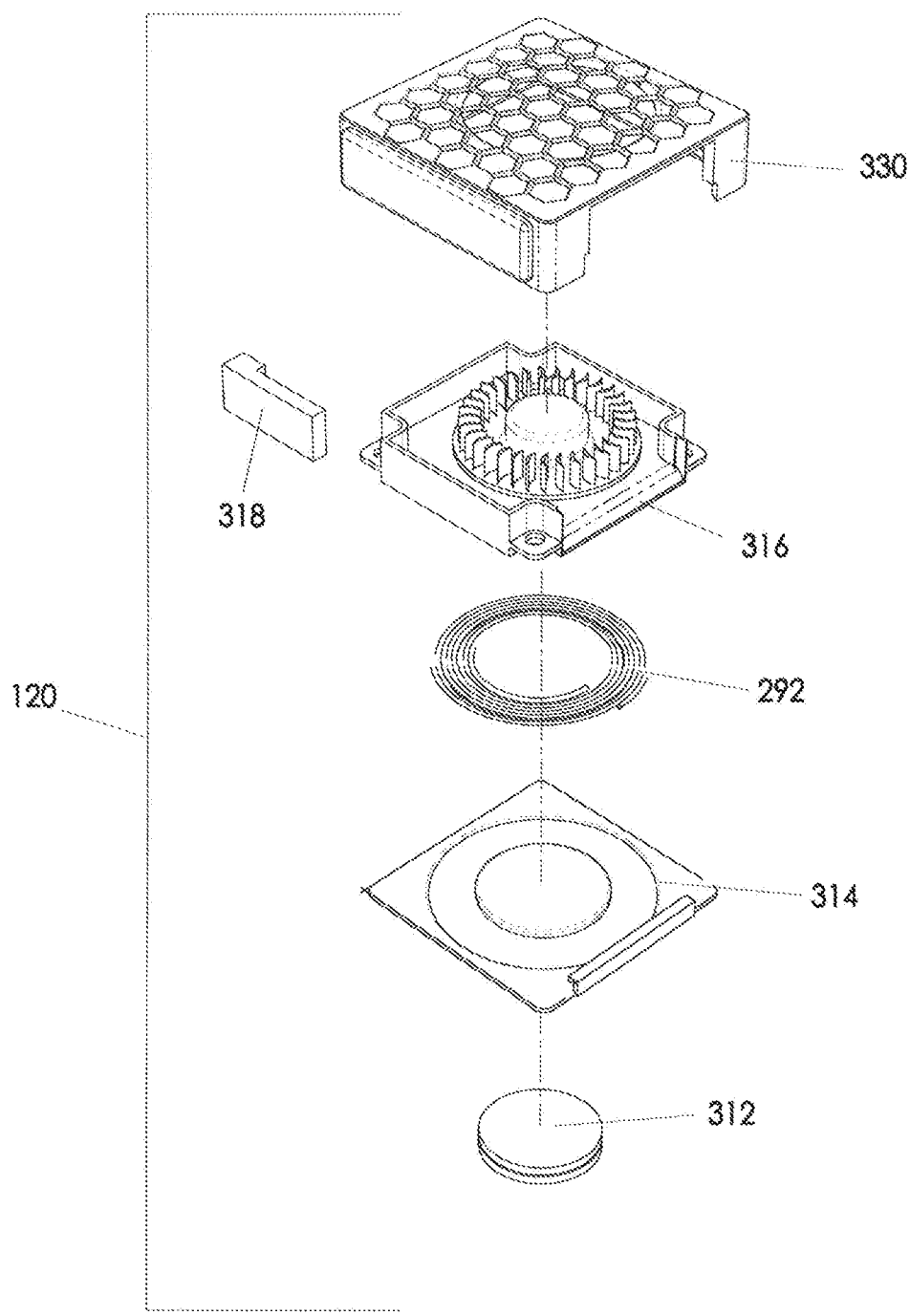
FIG. 10 depicts an exploded, perspective view of a second fan assembly 120 for use with the airflow assembly 100 of this invention.
Figure 11:
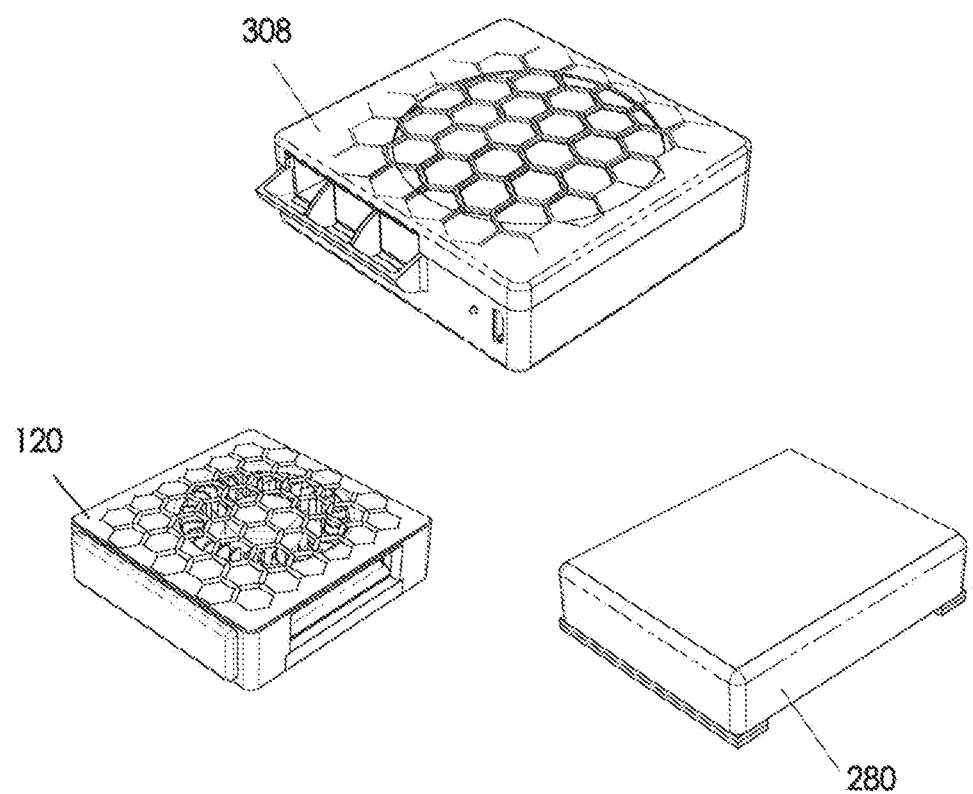
FIG. 11 depicts an assembled, perspective view of a first fan assembly 308, wireless battery assembly 280 and second fan assembly 120 all for use with the airflow assembly 100 of this invention.

Adding FIG. 8, FIG. 10 and FIG. 11 to the consideration, first fan assembly 308 for the airflow assembly 100 has one preferred structure shown. Operation of the first fan assembly 308 is facilitated by fan housing 310. Fan housing 310 includes bottom fan cover 314 and top fan cover 330. Within the bottom fan cover 314 and top fan cover 330 is receiving coil 292 followed by fan battery 334 and blower fan 316.

While fan battery 334 powers the fan assembly 308 without the battery assembly 280, the battery assembly 280 permits fan assembly 308 to run longer. The interior lateral wall 336 of bottom fan cover 314 also has attached to it control board 318, which includes micro switchboard 322 and switch mechanism 324, which functions to turn fan assembly 308 on or off. Above blower fan 316 is placed filter compartment 326 and filter medium 328, to improve air quality. The fan housing interior 340 of the bottom fan cover 314 and the fan housing exterior 344 support the fan assembly 308 in working order.

Adding FIG. 9 and FIG. 11, to the consideration, the wireless battery assembly 280 for the airflow assembly 100 is defined. The battery housing 278 supports wireless battery assembly 280 for connection to fan assembly 308 (FIG. 8). The wireless battery assembly 280 has battery fastener 282 to secure the battery housing 278 to a desired surface as shown in FIG. 2, FIG. 4 or FIG. 6. Battery fastener 282 can be Velcro (above defined) or a magnet (above defined).

Battery housing 278 includes battery top cover 204 and battery cover bottom 286. Fastener 282 is on battery cover bottom 286.

Transmitting coil 290 is between battery cover bottom 286 and battery shield 288. The external battery cover 294 is adjacent to battery shield 288. Battery 296 is between battery top cover 204 and battery shield 288. With battery top surface 284 on battery top cover 204, solar panel 332 can be mounted on battery top surface 284 to keep battery 296 permanently charged during daily use.

Considering FIG. 10 further, second fan assembly 120 includes top fan cover 330 adjacent to blower fan 316. Control board 318 is connected to blower fan 316. Blower fan 316 is between receiving coil 292 and top fan cover 330. Bottom fan cover 314 is between receiving coil 292 and fan fastener 312.

FIG. 11 shows the assembled first fan assembly 308, the second fan assembly 120 and the battery assembly 280. The battery assembly 280 can work with either the second fan assembly 120 or the first fan assembly 308. Either structure permits the transmitting coil 290 and the receiving coil 292 to work together.

Figure 12:
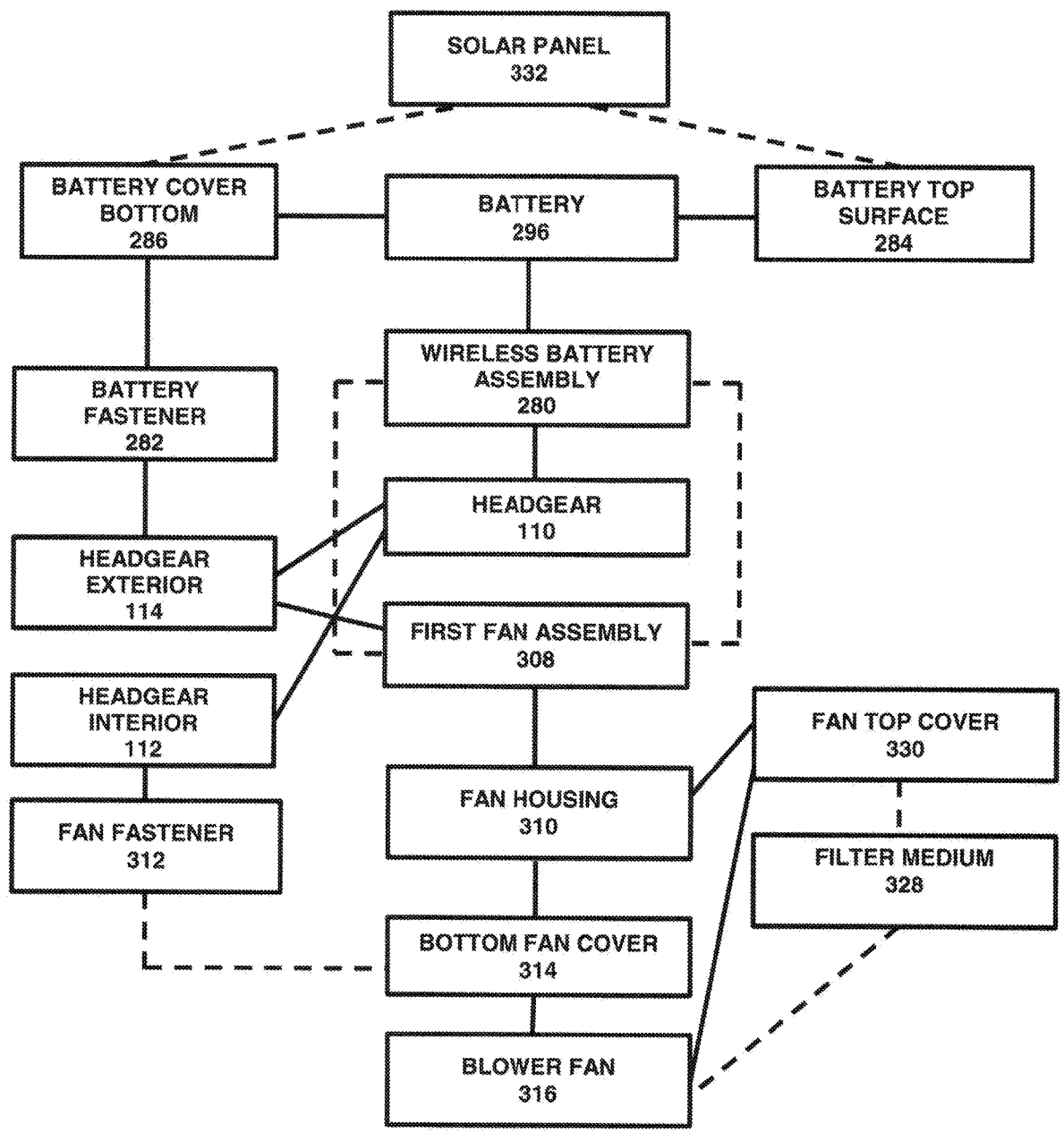
FIG. 12 depicts a second block diagram for the airflow assembly 100 of this invention.

Turning now to FIG. 12, airflow assembly 100 as a headgear 110, with a wireless battery assembly 280 and a fan assembly 308 attached thereto. The wireless battery assembly 280 and the fan assembly 308 cooperate to cool the wearer of headgear 110. Headgear 110 is worn on the head of a person, and may be hard or soft.

Battery fasteners 282 attach to headgear exterior 114 and battery cover bottom 286 to hold the battery assembly 280 in place by fan assembly 308, the fan assembly 208 being secured to headgear interior 112. Battery top surface 284 closes battery cover bottom 286 to hold the battery 296 within wireless battery assembly 280. Solar panel 332 may be placed on battery top surface 284 for the purpose of charging battery 296 of the wireless battery assembly 280. Thus battery 296 may be replaceable or rechargeable.

Fan assembly 308 and a fan housing 310 with the bottom fan cover 314 and the top fan cover 330. top fan cover 330 includes filter medium 228 and blower fan 360. Bottom fan cover 314 includes the fan housing 310. Fan fasteners 312 on bottom fan cover 314 secure the fan housing 310 to headgear interior 112.

This application; taken as a whole with the abstract, specification, claims, and drawings being combined; provides sufficient information for a person having ordinary skill in the art to practice the invention as disclosed and claimed herein. Any measures necessary to practice this invention are well within the skill of a person having ordinary skill in this art after that person has made a careful study of this disclosure.

Because of this disclosure and solely because of this disclosure, modification of this method and device can become clear to a person having ordinary skill in this particular art. Such modifications are clearly covered by this disclosure.

What is claimed and sought to be protected by Letters Patent of the United States is:

1. A lightweight and portable airflow assembly for increasing airflow comprising:
   an airflow mechanism forming the lightweight and portable airflow assembly designed for use within a headgear, wherein the headgear is a head covering;
   the airflow mechanism being of a size to be easily mounted on or placed within the headgear without discomforting a person wearing the headgear;
   the airflow mechanism being releasably attached to an interior of the headgear;
   the airflow mechanism being lightweight and portable;
   the airflow mechanism providing an airflow between the headgear and a head of the person wearing the headgear;
   the airflow mechanism including a fan assembly;
   the fan assembly including a blower fan, which causes an increased air intake and an increased air output between the interior of the headgear and the head of the person wearing the headgear, and being substantially contained within a fan housing, wherein the fan housing includes a top fan cover and a bottom fan cover, and the top fan cover and the bottom fan cover support the blower fan;
   a fan battery and a receiving coil cooperating to power a rotation function of the blower fan, the fan battery and the receiving coil being attached to an interior of the fan housing, and an exterior of the bottom fan cover being attached to the headgear interior; and
   a fan fastener releasably securing the fan housing on the interior of the headgear;
   wherein an entirety of the fan assembly is positioned in the headgear interior.

2. The lightweight and portable airflow assembly of claim 1 further comprising:
   the top fan cover communicating with a filter compartment;
   the filter compartment containing a filter medium; and
   the filter medium communicating with the air leaving the fan housing.

3. The lightweight and portable airflow assembly of claim 1 further comprising:
   the headgear being a welding mask, a hardhat, a police helmet, a first responder helmet, a military helmet, a baseball cap, or a cloth hat.

4. The lightweight and portable airflow assembly of claim 1 further comprising:
   a wireless battery assembly communicating with and providing power to the fan assembly to operate the fan assembly, wherein the wireless battery assembly is connected to the fan assembly; and
   the wireless battery assembly having at least one rechargeable battery therein.

5. The lightweight and portable airflow assembly of claim 4 further comprising:
   the receiving coil being within the bottom fan cover and the top fan cover;
   the receiving coil being adjacent to the fan battery and the blower fan;
   the fan battery being adapted to power the fan assembly without the wireless battery assembly;
   the wireless battery assembly permitting the fan assembly to run longer;
   the bottom fan cover having an interior lateral wall;
   a control board being attached to the interior lateral wall;
   the control board including a micro switchboard and a switch mechanism, which cooperate to turn the fan assembly on or off;
   the wireless battery assembly providing power to the fan assembly; and
   the blower fan being placed adjacent to the filter compartment and filter medium to improve air quality.

6. The lightweight and portable airflow assembly of claim 1, wherein the fan battery is rechargeable.

7. A lightweight and portable airflow assembly for increasing airflow comprising:

a fan assembly designed for use within a headgear, wherein the headgear is a protective head covering;

the fan assembly being of a size to be easily placed within the headgear without discomforting wearer;

the fan assembly being releasably attached to an interior of the headgear;

the fan assembly facilitating an air circulation of cooler air within the headgear by a rotation of fan blades;

a wireless battery assembly providing power for the rotation of fan blades;

the wireless battery assembly having a battery fastener releasably securing a battery housing to the headgear;

the battery housing having a battery cover top and a battery cover bottom, with a transmitting coil positioned between the battery cover top and the battery cover bottom and attached to the battery cover bottom;

the battery housing also having within it a battery shield between the transmitting coil and a battery, with the battery being placed between the battery shield and the battery cover top;

the fan assembly having a fan housing, with a bottom fan cover and a top fan cover;

the fan housing having within it a receiving coil between the bottom fan cover and a fan battery, a blower fan between the fan battery and a filter compartment, and a filter medium between the filter component and the top fan cover;

the battery cover top having attached thereto a solar panel; and the solar panel being a photovoltaic array wired to recharge the battery.

\* \* \* \* \*